United States Patent
Li et al.

(10) Patent No.: US 9,597,463 B2
(45) Date of Patent: Mar. 21, 2017

(54) INJECTION DEVICES WITH CONTROLLABLE DEPTH ADJUSTABILITY AND METHODS OF USE

(71) Applicant: Boston Scientific Scimed, Inc., Maple Grove, MN (US)

(72) Inventors: Jianmin Li, Lexington, MA (US); Timothy P. Harrah, Cambridge, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 239 days.

(21) Appl. No.: 14/209,606

(22) Filed: Mar. 13, 2014

(65) Prior Publication Data

US 2014/0276588 A1    Sep. 18, 2014

Related U.S. Application Data

(60) Provisional application No. 61/781,994, filed on Mar. 14, 2013.

(51) Int. Cl.
*A61M 5/178*     (2006.01)
*A61M 5/46*      (2006.01)
(Continued)

(52) U.S. Cl.
CPC .......... *A61M 5/46* (2013.01); *A61M 25/0084* (2013.01); *A61M 25/0097* (2013.01);
(Continued)

(58) Field of Classification Search
CPC ............ A61M 5/46; A61M 2025/0008; A61M 2025/0089; A61M 5/31501; A61M 2005/31508; A61M 5/31526
See application file for complete search history.

(56) References Cited

U.S. PATENT DOCUMENTS

| 3,799,406 A | 3/1974 | St. John et al. |
| 4,710,171 A | 12/1987 | Rosenberg |

(Continued)

FOREIGN PATENT DOCUMENTS

| DE | 297 08 149 U1 | 9/1997 |
| EP | 2 078 491 A1 | 7/2009 |
| WO | WO 2008/073214 A2 | 6/2008 |

OTHER PUBLICATIONS

International Search Report and Written Opinion for counterpart PCT Application No. PCT/US2014/026209 mailed Jul. 1, 2014 (12 pages).

*Primary Examiner* — Emily Schmidt
(74) *Attorney, Agent, or Firm* — Bookoff McAndrews, PLLC (57) ABSTRACT

An injection device for injecting a material into tissue may include a sheath having a distal end. The injection device may also include an injector having an outlet tube. The outlet tube may be received in the sheath, and may include a distal portion with a penetrating tip for penetrating the tissue. The sheath and the outlet tube may be slidable relative to each other, to extend a length of the distal portion from the distal end. The injection device may also include an adjuster operatively coupled to at least one of the sheath and the outlet tube. The adjuster may be configured to control relative movement between the sheath and the outlet tube for selectively adjusting the extended length.

19 Claims, 5 Drawing Sheets

(51) Int. Cl.
A61M 25/00 (2006.01)
*A61M 5/315* (2006.01)

(52) U.S. Cl.
CPC .... *A61B 2090/062* (2016.02); *A61M 25/0023* (2013.01); *A61M 2005/31508* (2013.01); *A61M 2025/006* (2013.01); *A61M 2025/0008* (2013.01)

(56) References Cited

U.S. PATENT DOCUMENTS

| | | | |
|---|---|---|---|
| 6,083,202 A * | 7/2000 | Smith | A61B 17/3478 604/164.01 |
| 6,126,633 A * | 10/2000 | Kaji | A61M 25/0084 604/164.01 |
| 6,200,291 B1 | 3/2001 | Di Pietro | |
| 6,585,694 B1 | 7/2003 | Smith et al. | |
| 7,811,254 B2 | 10/2010 | Wilmot et al. | |
| 7,927,271 B2 | 4/2011 | Dimitriou et al. | |
| 7,938,808 B2 | 5/2011 | Pessin | |
| 8,206,335 B2 | 6/2012 | Pruitt et al. | |
| 2001/0047151 A1 | 11/2001 | Xian et al. | |
| 2005/0187519 A1 | 8/2005 | Harris et al. | |
| 2007/0265579 A1 * | 11/2007 | Kleyman | A61C 5/062 604/207 |
| 2008/0097312 A1 | 4/2008 | Wilmot et al. | |

* cited by examiner

INJECTION DEVICES WITH CONTROLLABLE DEPTH ADJUSTABILITY AND METHODS OF USE

CROSS-REFERENCE TO RELATED APPLICATION

This application claims the benefit of U.S. Provisional Application No. 61/781,994, filed Mar. 14, 2013, the disclosure of which is incorporated herein by reference in its entirety.

TECHNICAL FIELD

Embodiments of the present disclosure generally relate to medical devices and procedures. In particular, embodiments of the present disclosure relate to injection devices with adjustable and controllable penetration depth and injection volume. These devices may be used in procedures involving the delivery of an injectable material into one or more target sites in a patient's body.

BACKGROUND

Botox bladder injections may be performed to treat neurogenic overactive bladder ("OAB"). Such injections may be appealing because the procedure does not require a permanent implant, is minimally invasive, and may provide several months of relief. Botox bladder injections may be done in a cystoscopically guided procedure, where a physician may inject Botox into twenty or thirty spots in a patient's bladder.

The efficacy of the procedure may depend on a number of factors. One of those factors is needle penetration depth. Another factor is injection quantity. A need exists for injection devices that offer control of needle penetration depth and quantity of material injected, with better precision than that offered by conventional injection devices.

SUMMARY

Embodiments of the present disclosure relate to, among other things, injection devices with controllable depth adjustability and methods of use. Each of the embodiments disclosed herein may include one or more of the features described in connection with any of the other disclosed embodiments.

In accordance with one aspect of the present disclosure, an injection device may provide easy and consistent multisite cystoscopic injections. The device may allow a needle, for penetrating tissue, to be advanced to one or more fixed positions to inject material into the tissue at a substantially constant depth (e.g., 0-10 mm). The device may also be configured to permit control of injection volume. The device may be used for the treatment of OAB by injecting a suitable material, such as saline, Botox, fluid/solid mixture and/or a gel. The device may provide consistency of depth and injection volume and ease-of use for reduction of procedure time by making repeated injections without the need to watch or further adjust the device. The average number of injections per bladder may be in the range of 20-30 injections per procedure, with a volume per injection of approximately 0.25 to 1 mL.

In accordance with another aspect of the present disclosure, an injection device for injecting a material into tissue may include a sheath having a distal end. The injection device may also include an injector having an outlet tube. The outlet tube may be received in the sheath, and may include a distal portion with a penetrating tip for penetrating the tissue. The sheath and the outlet tube may be slidable relative to each other, to extend a length of the distal portion from the distal end. The injection device may also include an adjuster operatively coupled to at least one of the sheath and the outlet tube. The adjuster may be configured to control relative movement between the sheath and the outlet tube for selectively adjusting the extended length.

In accordance with another aspect of the present disclosure, an injection device for injecting a material into tissue may include an injector. The injector may include a barrel having an internal chamber configured to hold the material. The injector may also include a tube fluidly coupled to the internal chamber and configured to receive material expelled from the internal chamber. The injector may also include a plunger slidably received in the internal chamber and configured to slide relative to the internal chamber to expel material from the internal chamber. The injector may also include a guiding element configured to engage the plunger to restrict movement of the plunger. The plunger may include a plurality of notches. The guiding element may be configured to selectively engage at least one of the plurality of notches. The injection device may also include an adjuster coupled to the injector, the adjuster being configured to selectively adjust a desired depth of penetration of the tube into the tissue.

In accordance with another aspect of the present disclosure, a method of injecting predetermined amounts of a material at a predetermined depth in a plurality of sites of a portion of tissue, may include moving one of a tube and a sheath at least partially surrounding the tube, relative to the other of the tube and the sheath, to expose a length of a distal portion of the tube from a distal end of the sheath. The method may also include coupling the tube and the sheath to fix the exposed length of the distal portion of the tube, and set the predetermined penetration depth of the distal portion of the tube into the portion of tissue. The method may also include penetrating a first site of the portion of tissue with the exposed length of the tube. The method may also include actuating an injector to inject a predetermined amount of the material into the portion of tissue at the first site. The method may also include withdrawing the exposed length of the tube from the first site of the portion of tissue.

Additional objects and advantages of the disclosure will be set forth in part in the description which follows, and in part will be obvious from the description, or may be learned by practice of the disclosure.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 3 shows a front view of a flange of the injection device in FIG. 1, according to an exemplary embodiment of the present disclosure;

FIGS. 9A-9C show back, side, and bottom views of a holder of the injection device in FIG. 7, according to an exemplary embodiment of the present disclosure;

DETAILED DESCRIPTION

Overview

The present disclosure is drawn to injection devices with controllable and adjustable penetration depth and injection volume, and methods of use. Reference will now be made in detail to exemplary embodiments of the disclosure, examples of which are illustrated in the accompanying drawings. The same reference numbers will be used throughout the drawings to refer to the same or like parts. Also, any aspect set forth in any embodiment may be used with any other embodiment set forth herein.

The terms "proximal" and "distal" are used herein to refer to the relative positions of the components of the exemplary injection devices. When used herein, "proximal" refers to a position relatively closer to the surgeon using the exemplary injection devices. In contrast, "distal" refers to a position relatively further away from the surgeon using the exemplary injections devices, or closer to a surgical site located within a patient's body.

Exemplary Embodiments

An exemplary injection device 10 is shown in FIGS. 1-6. The injection device 10 may include an injector 12, a base 14, a sheath 16, an adjuster 17, and a depth indicator 18. The injector 12, base 14, sheath 16, adjuster 17, and depth indicator 18 are described in more detail below.

Figure 1:
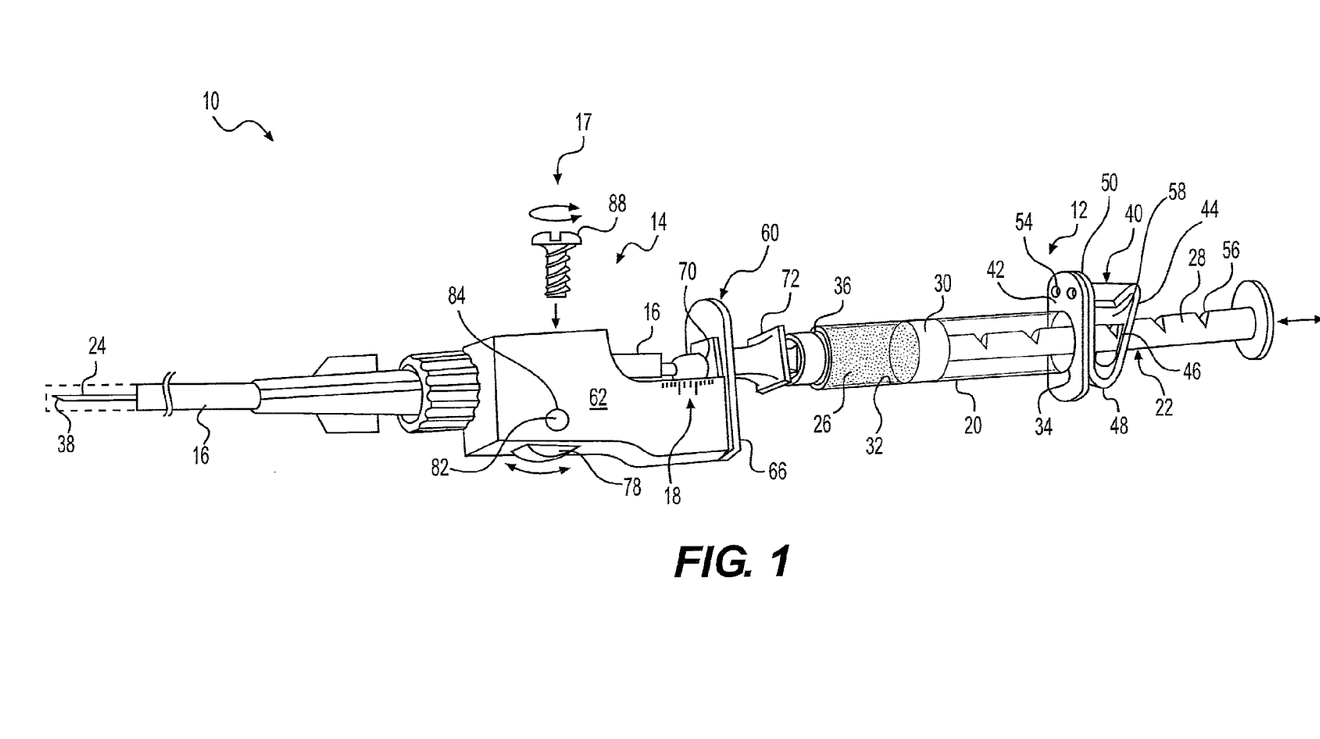
FIG. 1 shows a perspective view of an injection device, according to an exemplary embodiment of the present disclosure.
Figure 2A:
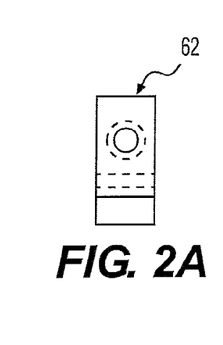
FIGS. 2A-2E show front, top, side, bottom, and back views of a housing of the injection device in FIG. 1, according to an exemplary embodiment of the present disclosure.
Figure 2B:
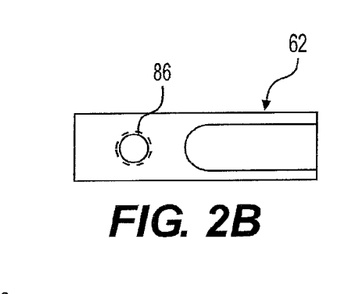
Figure 2C:
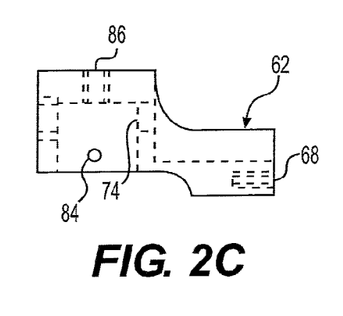
Figure 2D:
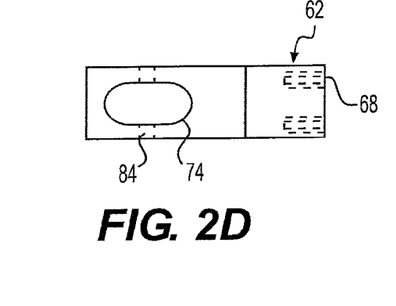
Figures 2E, 4A:
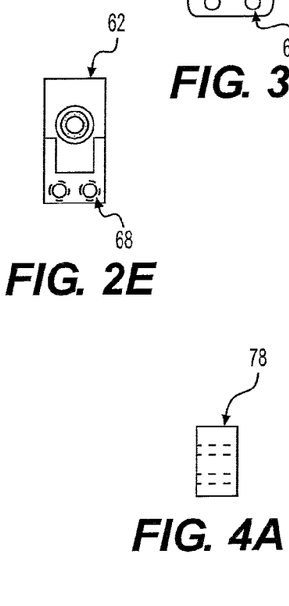
FIGS. 4A and 4B show front and side views of a roller of the injection device in FIG. 1, according to an exemplary embodiment of the present disclosure.
Figure 4B:
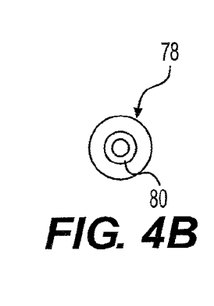

The injector 12 may form a proximal end of the injection device 10. The injector 12 may include a barrel 20, a plunger 22, and a tube, such as a polymeric or metallic hypotube 24.

The injector 12 may be configured to receive material 26, and when actuated, the injector 12 may deliver the material 26 to one or more sites. The material may include, for example, Botox, a bulking material, saline, and/or a gel.

The plunger 22 may include a shaft 28 forming a proximal end of the plunger 22, and a seal 30 forming a distal end of the plunger 22. The seal 30 may be coupled to a distal end of the shaft 28. The seal 30 may be sized and configured to be received in an internal chamber 32 of the barrel 20. An outer surface of the seal 30 may slidably engage and form a seal with a surface of the internal chamber 32.

The internal chamber 32 of the barrel 20 may hold the material 26. A proximal end of the barrel 20 may include an opening 34 for receiving at least a portion of the plunger 22, such as the seal 30 and/or a portion of the shaft 28. The distal end of the barrel 20 may include an opening 36, putting the barrel 20 in fluid communication with the hypotube 24. The material 26 may be loaded into the barrel 20 through either of the proximal and distal openings 34 and 36, and may be discharged from the barrel 20 into the hypotube 24 by pushing the plunger 22 in a distal direction.

The distal end of the barrel 20 may be coupled to a proximal end of the hypotube 24. A distal end of the hypotube 24 may include a penetrating tip 38 configured to penetrate tissue and/or other materials. For example, the penetrating tip 38 may include a needle grind and/or bevel for ease of penetration. The hypotube 24 may be sufficiently flexible to bend in one or more planes as the penetrating tip 38 of the hypotube 24 is navigated through one or more body passages to a target area in a patient's body.

When the material 26 is in the barrel 20, moving the plunger 22 distally may force the material 26 out of the barrel 20, into the hypotube 24, through the hypotube 24, and out of the penetrating tip 38 of the hypotube 24. The distance the plunger 22 moves distally may be indicative of the amount of the material 26 expelled from the penetrating tip 38 of the hypotube 24. Accordingly, by controlling movement of the plunger 22, the amount of material expelled from the penetrating tip 38 may be controlled.

Figure 5A:
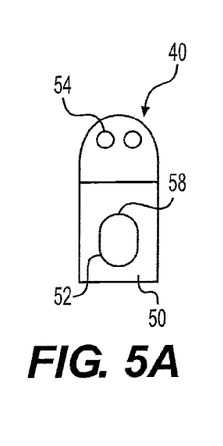
FIGS. 5A and 5B show front and side views of a guide element of the injection device in FIG. 1, according to an exemplary embodiment of the present disclosure.
Figure 5B:
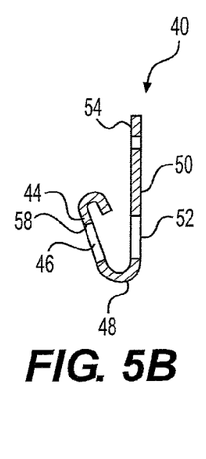

The barrel 20 may include a guide element 40 configured to assist with controlling movement of the plunger 22, and thus, the amount of the material 26 that is expelled from the penetrating tip 38. The guide element 40 may be a spring clip attached to a flange 42 of the barrel 20 that at least partially surrounds the proximal opening 34. The guide element 40 may include a proximal leg 44 with a proximal aperture 46, a bend 48, and a distal leg 50 with a distal aperture 52 (FIGS. 5A and 5B). The distal leg 50 may be attached to the flange 42 by an attachment mechanism 54. The attachment mechanism 54 may include, for example, one or more mechanical fasteners, one or more adhesives, and/or any other conventional attachment mechanism known in the art.

The guide element 40 may be configured to selectively engage notches 56 on the plunger shaft 28. For example, a lip 58 defining a part of the proximal aperture 46 may engage one of the notches 56 when the guide element 40 is in a first position. When a user applies enough force on a proximal end of the plunger 22, in the distal direction, a proximal surface of the notch 56 may engage the lip 58. Engagement between the proximal surface of the notch 56 and the lip 58 may push the proximal leg 44 toward the distal leg 50, causing bending at the bend 48, resulting in the proximal leg 44 moving distally with a pivoting motion. The depth of the lip 58 into the notch 56 is configured to allow the user to continue to apply the force, pivoting the proximal leg 44, and at some point, allowing the lip 58 to escape the notch 56 and contact an area or surface of the shaft 28 between the notches 56. As the user continues to depress the plunger 22, the lip 58 may enter and engage an adjacent notch 56. When this happens, the proximal leg 44 may move back to its first position. Engagement of the lip 58 with the adjacent notch 56 may produce a clicking sound and/or tactile sensation providing the user with an indication that the plunger 22 has been moved a distance substantially equal to the distance between adjacent notches 56. The engagement may also help prevent undesired overtravel of the plunger 22 by offering some resistance to movement of the plunger 22.

The distance travelled by the plunger 22 in the distal direction may be indicative of the amount of the material 26 expelled from the penetrating tip of the hypotube 24. By increasing the distance between adjacent notches 56, more of the material 26 is expelled between clicks. By decreasing the distance between adjacent notches 56, less of the material 26 is expelled between clicks. The distances between adjacent notches 56 on the plunger shaft 28 may be equal, so the same amounts of the material 26 can be injected one after another by pushing the plunger shaft 28 until sensing a subsequent click, and then repeating. If, for some reason, the serial injection of different amounts of the material 26 is desired, the plunger 22 may be provided with adjacent notches 56 that are not equally-spaced.

It is also contemplated that a single plunger 22 may include a first group of linearly arranged notches 56, having a first distance between each of the notches 56, along a first side of the shaft 28, such as the top side in FIG. 1; and a second group of linearly arranged notches (not shown), having a second distance between each of the notches, along a second side of the shaft 28, such as the left, right, and/or bottom side in FIG. 1. First amounts of the material 26 may be expelled from the penetrating tip 38 of the hypotube 24, between clicks, by rotating the plunger 22 to align the first group of notches 56 with the lip 58, and then forcing the plunger 22 distally. Second amounts of the material 26 may be expelled from the penetrating tip 38 of the hypotube 24, between clicks, by rotating the plunger 22 to align the second group of notches 56 with the lip 58, and then forcing the plunger 22 distally. It is also contemplated that the injection device 10 may come with a plurality of different plunger shafts in a kit, and the user may select a particular plunger shaft from the kit based on the type of procedure and desired injection amounts the user intends to perform with the injection device 10.

In an alternative embodiment, an O-ring may be provided in place of the guide element 40. The O-ring may have an inner diameter similar to an outer diameter of the shaft 28 of the plunger 22, and an outer diameter large enough to engage the flange 42 to prevent entry of the O-ring into the barrel 20. The O-ring may remain in contact with the flange 42 as the plunger 22 is pushed distally, and may engage each of the notches 56 as they pass through the inner surface of the O-ring. Alternatively, the shaft 28 of the plunger 22 may include markings instead of the notches 56. A user may press the plunger 22 distally until an adjacent marking reaches the O-ring. By repeating this action, predetermined amounts of the material 26 may be injected.

Alternatively, the guide element 40 may be replaced by any suitable arrangement of clamps, clips, pins, or ratchets. For example, the shaft 28 of the plunger 22 may be provided with a set of linearly arranged ratchet teeth, configured to engage a spring-biased pawl provided on the barrel 20 near, for example, the flange 42. Each of the teeth may include a moderately sloped distal surface, sloping away from a longitudinal axis of the shaft 28 in a proximal direction, and a proximal surface with a steeper slope extending from a proximal side of the sloped surface. The pawl may engage a space defined by the steeply sloped surface of a ratchet tooth and the moderately sloped surface of a proximally adjacent ratchet tooth. As the plunger 22 is depressed distally, the pawl may engage the moderately sloped surface of the proximally adjacent ratchet tooth, until the pawl reaches the steeply sloped surface of the proximally adjacent ratchet tooth. As the pawl traverses the steeply sloped surface, the pawl will move back toward the longitudinal axis of the shaft 28 and rest in the space defined by the steeply sloped surface and the moderately sloped surface of the next proximally adjacent ratchet tooth. Moving the plunger 22 to cause movement of the pawl from space to space may help a user inject predetermined amounts of the material 26 during each of a plurality of injections.

Alternatively, any suitable system for dispensing predetermined amounts of material may be used in place of the injector 12. For example, a reciprocating injector may be used. In a reciprocating injector, a plunger may move into a proximal position, and material may be loaded into a barrel from a reservoir. A one-way valve may be positioned between the barrel and the reservoir, the one-way valve being configured to allow the material to flow from the reservoir into the barrel, and prevent the material from flowing from the barrel back into the reservoir. When the user presses the plunger to a distal position, the material may be expelled from a tip of a needle. A one-way valve may be positioned between the barrel and the needle, the one way valve being configured to allow the material to flow from the barrel to the needle, and prevent the material from flowing from the needle back into the barrel. A spring force acting on the plunger may move the plunger proximally back to the first position, creating a vacuum force in the barrel, the vacuum force drawing more of the material into the emptied barrel from the reservoir. This cycle may be repeated to make consecutive substantially similar injections of the material. It is also contemplated that a powered pumping device may be used to supply desired amounts of the material.

It is also contemplated that the plunger 22 may be a screw-type plunger. For example, a region of the outer surface of the plunger 22 may be substantially cylindrical, and may include external threads (not shown). A region of the barrel 20 may include internal threads (not shown) configured to engage the external threads. For example, the external threads may be positioned on an outer surface of the shaft 28, and the internal threads may be positioned on a member (not shown) extending from a surface of the barrel 20, the member including an opening with the internal threads. Rotation of the plunger 22 relative to the barrel 20 may produce longitudinal movement of the plunger 22, due to engagement between the internal and external threads. By counting the number of rotations of the plunger 22 relative to the barrel 20, a user may determine how much of the material 26 has been injected, since the number of rotations corresponds to the longitudinal distance covered by the plunger 22 during rotation of the plunger 22. Thus, the user may control the quantity of the material 26 injected by controlling the number of rotations of the plunger 22 relative to the barrel 20, that the user performs during a procedure.

The injector 12 may be coupled to a proximal end of the base 14, the hypotube 24 may extend through the base 14, and the sheath 16 may be slidably coupled to a distal end of the base 14. The base 14 may include a receiver 60 (FIGS. 1 and 3), a housing 62 (FIGS. 2A-2E), and the adjuster 17 (FIGS. 1, 4A, 4B, and 6).

The receiver 60 may include a flange 66 coupled to a proximal end of the housing 62 by, for example, any suitable attachment arrangement 68 like screws and corresponding screw holes, adhesives, and the like (FIG. 3). The flange 66 may include an opening 70 (FIG. 3) for receiving and supporting a funnel 72. A proximal end of the funnel 72 may receive the hypotube 24 and/or the distal end of the injector 12.

The hypotube 24 may be inserted through the funnel 72, into the housing 62, from the proximal end of the housing 62, and the sheath 16 may be inserted through the distal end of the housing 62. The hypotube 24 and the sheath 16 may pass through one or more passages 74 in the housing 62. Within the one or more passages 74 of the housing 62, the hypotube 24 may enter a proximal end of the sheath 16. The sheath 16 and the hypotube 24 may extend distally out of the housing 62. The penetrating tip 38 of the hypotube 24 may be located at or near the distal end of the sheath 16.

Figure 6:
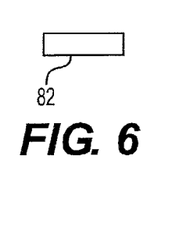
FIG. 6 shows a front view of a pin of the injection device in FIG. 1, according to an exemplary embodiment of the present disclosure.

The adjuster 17 may be occupy at least a portion of the passage 74 of the housing 62. The adjuster 17 may include a roller 78 (FIGS. 4A and 4B), which may be made of rubber. The roller 78 may include a bushing 80 (FIG. 4B) configured to receive a dowel pin or axle 82 (FIG. 6). The axle 82 may be supported at its ends by axle holes 84 extending in the housing 62. The roller 78 may rotate, relative to the housing 62, about the axle 82. The axle holes 84 may be positioned so that at least a portion of the roller 78 protrudes from a surface of the housing 62. Within the housing 62, an upper surface of the roller 78 may engage a lower surface of the sheath 16.

A hole 86 in the housing 62 may open into the passage 74. A screw 88 of the adjuster 17 may be inserted through the hole 86, which may be a threaded hole, and into the passage 74. As the screw 88 is rotated in a first direction, the screw 88 may travel deeper into the passage 74. As the screw 88 is rotated in the first direction, a lower surface of the screw 88 may engage the sheath 16, press the sheath 16 against the hypotube 24, and press the sheath 16 and the hypotube 24 against the roller 78. When the clamping force exerted on the sheath 16 and the hypotube 24 by the screw 88 against the roller 78 reaches a threshold, relative movement between the sheath 16 and the hypotube 24 may be prevented.

It is also contemplated that clamping of the sheath 16 may be accomplished without the screw 88 and the roller 78. For example, the screw 88 and the roller 78 may be replaced by a clamp (not shown) that may be actuated by a cam (not shown), wherein movement of the cam may actuate the clamp to exert a clamping force on the sheath 16 and the hypotube 24. Alternatively, the screw 88 may be replaced by a ramp or wedge (not shown) that may be movable toward and away from the roller 78, to clamp and unclamp the sheath 16 and the hypotube 24. Alternatively, the screw 88 may be replaced by a sliding pin (not shown) that may be moved toward and into contact with the sheath 16 and the hypotube 24, to exert a clamping force thereon. It should be understood that any suitable clamping mechanism may be used to clamp the sheath 16 and the hypotube 24.

Reducing the clamping force, by, for example, rotating the screw 88 in a second direction to unscrew the screw 88, may lighten the clamping force enough to allow relative movement between sheath 16 and the hypotube 24. For example, when the clamping force is low enough, a user may rotate the roller 78 using the lower portion of the roller 78 that protrudes from the lower surface of the housing 62. When the roller 78 is rotated in a clockwise direction, the sheath 16 may move proximally relative to the hypotube 24 due to frictional engagement between the top surface of the roller 78 and the lower surface of the sheath 16. This may cause the penetrating tip 38 of the hypotube 24 to be exposed from the distal end of the sheath 16. When the roller 78 is rotated in a counterclockwise direction, the sheath 16 may be moved distally relative to the hypotube 24, causing the penetrating tip 38 of the hypotube 24 to be covered by the distal end of the sheath 16.

In an alternative embodiment, the sheath 16 may include a region of its outer surface that may have external threads (not shown), and the housing 62 may include a region of its inner surface that may have internal threads (not shown). Additionally or alternatively, the sheath 16 may include a proximal adapter (not shown) with the external threads, while the housing 62 may include an opening, defined by a portion of the housing 62, with the internal threads. The external and internal threads may form a screw-type engagement mechanism. That is, as the sheath 16 is rotated relative to the housing 62, the external and internal threads will engage, converting the relative rotation into longitudinal movement of the sheath 16 relative to the hypotube 24. The longitudinal movement may be used to expose and cover the penetrating tip 38 of the hypotube 24. It is also contemplated that the proximal adapter may be substantially cylindrical, and free of threads. The proximal adapter may slide within the housing 62, to move the sheath 16, and may be fixed in desired positions by engaging the proximal adapter with the screw 88.

The depth indicator 18, in the form a gauge and/or ruler-type markings, may be provided on the housing 62, to provide an indication of the position of the proximal end of the sheath 16 relative to the housing 62, and thus, an indication of the length of the hypotube 24 that is extending out from the distal end of the sheath 16. The length of the hypotube 24 that extends out from the distal end of the sheath 16 may be substantially equal to the penetration depth of the hypotube 24 into the tissue. This is because the distal end of the sheath 16 may form a stop, inhibiting further penetration of the hypotube 24 into the tissue. Thus, by using the depth indicator 18, the screw 88, and the roller 78, a user may selectively set and adjust needle penetration depth, with accuracy, from outside the patient's body. The depth indicator 18 may be calibrated by, for example, determining the gauge marking at which the proximal end of the sheath 16 falls when the penetrating tip 38 of the hypotube 24 is at the distal end of the sheath 16, and using that as a reference point for comparison when the proximal end of the sheath 16 moves to a different gauge marking. The difference between the gauge markings may be indicative of the movement of the hypotube 24 relative to the sheath 16, and thus, needle penetration depth.

Additionally or alternatively, a depth indicator, similar to the depth indicator 18, may be provided on or coupled to the sheath 16. For example, the depth indicator may include printed material, raised regions, and/or recessed regions on the sheath 16, or on a body coupled to the sheath 16. During proximal movement of the sheath 16, markings on the sheath 16 or the body may be exposed after having been obscured by, for example, part of the housing 62. The number/type of markings exposed may provide the user with an indication of how far proximally the sheath 16 has been moved, and thus, how much of the distal portion of the hypotube 24 is exposed. The markings may include ruler type markings, digits, text and/or any other suitable indicators. It is contemplated that the housing 62 may include a window (not shown), for viewing the markings, with the window exposing the marking or markings that are indicative of sheath 16 movement and hypotube 24 exposure, and obscuring the other markings. As the sheath 16 is moved, the markings may travel through the window.

Additionally or alternatively, a depth indicator, similar to the depth indicator 18, may be coupled to the hypotube 24. For example, the depth indicator may include printed material, raised regions, and/or recessed regions on a body coupled to the hypotube 24. During proximal movement of the sheath 16, markings on the body may be exposed after having been obscured by, for example, part of the housing 62. The number/type of markings exposed may provide the user with an indication of how much of the distal portion of the hypotube 24 is exposed. The markings may include ruler type markings, digits, text and/or any other suitable indicators. It is contemplated that the housing 62 may include a window (not shown), for viewing the markings, with the window exposing the marking or markings that are indicative of hypotube 24 exposure, and obscuring the other markings. As the sheath 16 is moved, the markings may travel through the window.

During use of the injection device 10, the injector 12, the base 14, and the sheath 16, may be arranged, as shown in FIG. 1, while the injection device 10 is outside of a patient's body. The penetrating tip 38 of the hypotube 24 may be positioned at the distal end of the sheath 16, so the penetrating tip 38 of the hypotube 24 does not protrude from the distal end of the sheath 16. The screw 88 may be tightened to clamp the sheath 16 and the hypotube 24 against the roller 78. This may prevent the hypotube 24 from moving relative to the sheath 16, and thus, prevent the penetrating tip 38 from exiting from the distal end of the sheath 16 prematurely.

The sheath 16 may be inserted through a lumen (not shown). The lumen may include a body lumen, or an artificial lumen in a steerable catheter, scope, or similar device (not shown). The distal end of the sheath 16, and the penetrating tip 38 of the hypotube 24 within the sheath 16, may be navigated to a target area in the patient's body. Once the target area is reached, the user may unscrew the screw 88 to release the clamping force acting on the hypotube 24 and the sheath 16. The user may retract the sheath 16 proximally, by rolling the roller 78, to expose a desired length of the hypotube 24 from the sheath 16. The user may use the depth indicator 18 to help determine how much of the hypotube 24 is exposed. When the desired amount of exposure achieved, the user may screw the screw 88 back in to clamp the sheath 16 and the hypotube 24 between the screw 88 and the roller 78, thereby locking the sheath 16 to the hypotube 24, and fixing the exposed length of the hypotube 24.

With the exposed length of the hypotube 24 set, the user may penetrate tissue at a first site in the target area, with the exposed portion of the hypotube 24, until the tissue abuts the distal end of the sheath 16 and prevents further penetration. This may be assisted using conventional imaging devices at the distal end of the scope. The user may then push the plunger 22 distally until a click is sensed to dispense a predetermined quantity of the material 26 into the first site. The user may withdraw the exposed portion of the hypotube 24 from the first site, and insert the exposed portion of the hypotube 24 into tissue at a second site in the target area, until the distal end of the sheath 16 prevents further penetration. Since the exposed length of the hypotube 24 is fixed, the penetration depth of the hypotube 24 in the two sites site may be substantially equal. The user may then push the plunger 22 distally until a click is sensed, thus injecting a quantity of the material 26 into the second site that is substantially equal to the quantity of material 26 injected into the first site. This cycle may be repeated a plurality of times at subsequent sites to consistently inject the same quantity of the material 26 at the same injection depth, in a plurality of different injection sites.

While consistency may be desirable for some types of procedures, it should be understood that, if desired, a user may change the length of exposed hypotube 24 to achieve a different penetration depth, and/or change the distance between notches 56 on the plunger 22 to achieve a different injection quantity, at any time before, during, and/or after insertion of the injection device 10 into the body.

The injection device 10 may be used to treat OAB in a patient using the steps described above. To treat OAB, the injection device 10 may be inserted to a target area in a patient's bladder using, for example, a cystoscope (not shown). At the target area, the penetration depth may be set at a depth of 10 mm (or less/more, depending on what is deemed suitable by the user). The injector 12 may be configured to delivery 0.25 to 1 mL of saline, botox, fluid/solid mixture or gel, as the plunger 22 moves between adjacent notches 56. With the injection device 10 positioned and set, the user may deliver 20-30 injections in target sites of the bladder per procedure. However, it should be understood that the injection device 10, and its methods of use, may be employed in other areas of a patient's body, including within other organs.

Another exemplary injection device 90 is shown in FIGS. 7-13. The injection device 90 may include the injector 12 and the sheath 16, and a base 92. The hypotube 24 may extend through the base 92 and into the sheath 16. The base 92 may include a receiver 94, a housing 96, an adjuster 98, and a depth indicator 100. The receiver 94 may be located at a proximal end of the base 92. The sheath 16 may be coupled to the distal end of the base 92.

Figure 10A:
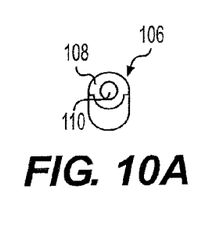
FIGS. 10A-10C show back, side, and bottom views of a mounting member of the injection device in FIG. 7, according to an exemplary embodiment of the present disclosure.
Figure 10B:
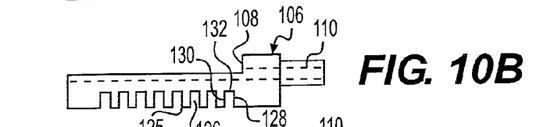
Figure 10C:
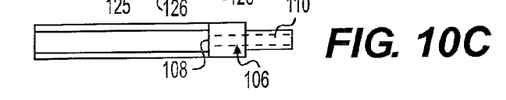

The receiver 94 may include an adapter 102, including a central passage 104 configured to receive a distal end of the injector 12 and the hypotube 24. The adapter 102 may be coupled to a mounting member 106 (FIGS. 10A-10C). For example, a distal portion of the adapter 102 may be slid in a distal direction on a top surface of the mounting member 106, the top surface having a shape complementary to a shape defined by the outer surface of the adapter 102, until a distal end of the adapter 102 abuts a shoulder 108 of the mounting member 106. The shoulder 108 may include an opening 110 configured to allow passage of the hypotube 24. The adapter 102 and the mounting member 106 may be coupled using any suitable attachment mechanism, and when coupled, the adapter 102 and the mounting member 106 may be fixed relative to one another.

The mounting member 106 may be received in a holder 111 (FIGS. 9A-9C), and the holder 111 may be received in a passage 112 in the housing 96. The mounting member 106 may be slidable, along proximal and distal directions, relative to the holder 111 and within the passage 112. Because the injector 12 and the mounting member 106 may be coupled, distal sliding of the mounting member 106 relative to the housing may correspond to distal movement of the injector 12 and the hypotube 24 relative to the housing 96. Similarly, proximal sliding of the mounting member 106 relative to the housing corresponds to proximal movement of the injector 12 and the hypotube 24 relative to the housing 96.

Figure 7:
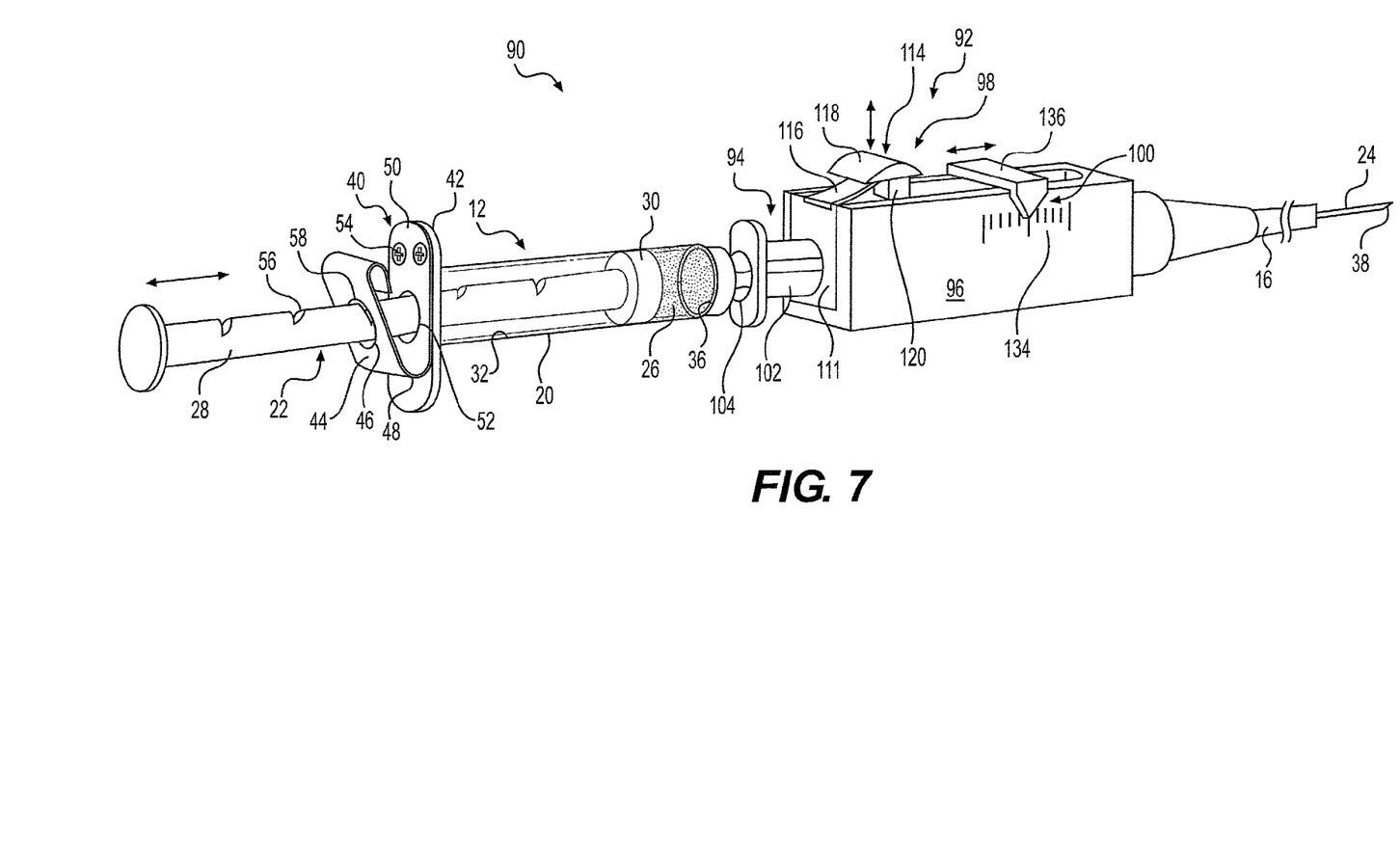
FIG. 7 shows a perspective view of another injection device, according to an exemplary embodiment of the present disclosure.

The distal end of the housing 96 may be coupled to the proximal end of the sheath 16. It is contemplated that in this embodiment, there may be no relative sliding between the housing 96 and the sheath 16. Thus, the sheath 16 may not be withdrawn to expose the penetrating tip 38 of the hypotube 24, or extended to cover the penetrating tip 38. Rather, the sheath 16 remains fixed with respect to the housing 96, but the mounting member 106 and the injector 12 may slide in the passage 112 of the housing 96, resulting in proximal or distal movement of the hypotube 24 (coupled to the injector 12) relative to the sheath 16 (coupled to the housing 96). Moving the hypotube 24 distally relative to the sheath 16 may extend a distal portion of the hypotube 24 from the distal end of the sheath 16, and moving the hypotube 24 proximally relative to the sheath 16 may retract a proximal portion of the hypotube 24 into the distal end of the sheath 16. The length of the distal portion of the hypotube 24 extending out from the distal end of the sheath 16 may correspond to the penetration depth of the hypotube 24 into tissue. By setting the position of the mounting member 106 relative to the housing 96, the length of the hypotube 24 that extends out from the sheath 16 can be set, thereby setting the penetration depth of the hypotube 24 into the tissue.

Figure 13:
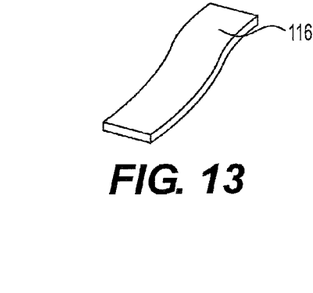
FIG. 13 shows a perspective view of a button spring of the injection device in FIG. 7, according to an exemplary embodiment of the present disclosure.

The position of the mounting member 106 relative to the housing 96 may be set and/or adjusted. The setting and/or adjusting may involve incremental movements of the mounting member 106. This may be achieved using the adjuster 98. The adjuster 98 may be at least partially located in the passage 112. The adjuster 98 may include a locking button 114 (FIGS. 11A-11C) and a button spring 116 (FIG. 13). The locking button 114 may include a head 118 accessible from outside of the housing 96, and a locking element 120 extending from the head 118 into the housing 96. The button spring 116 may be coupled to one end of the housing 96, and on the opposite end to the locking button 114 at, for example, an underside of the head 118 and/or a side surface of the locking element 120. The button spring 116 may bias the locking button 114 in an upward direction in FIG. 3. A force may be applied to the head 118, in a downward direction, to overcome the spring bias of the button spring 116, forcing the locking button 114 further into the housing 96.

Figures 8A, 8C:
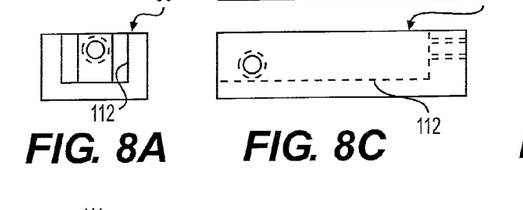
FIGS. 8A-8D show back, top, side, and front views of a housing the injection device in FIG. 7, according to an exemplary embodiment of the present disclosure.
Figure 8B:
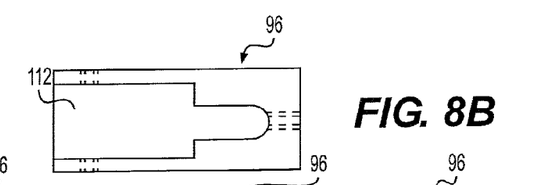
Figures 8D, 11A:
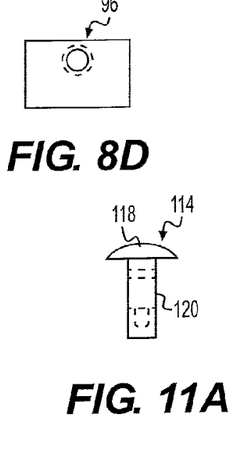
FIGS. 11A-11C show side, front, and partial section views of a locking button of the injection device in FIG. 7, according to an exemplary embodiment of the present disclosure.
Figure 11B:
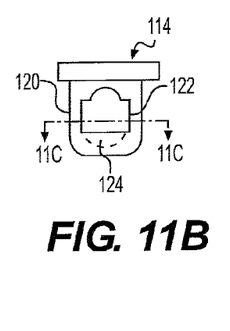
Figure 11C:
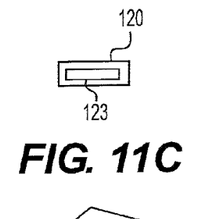

The locking element 120 may include an opening 122 and a slot 123 (FIGS. 11A-11C). When a downward force applied to the head 118 of the locking button 114 overcomes the spring bias exerted by the button spring 116, the locking button 114 may move to a lowered position, such that the opening 122 in the locking element 120 is substantially aligned with the periphery of the mounting member 106. In this state, the mounting member 106 can pass through the opening 122 substantially unimpeded. When the downward force is reduced or removed, the button spring 116 may force the locking button 114 upward, shifting the opening 122 upward and bringing the slot 123 of the locking element 120 over one of the protrusions 125, and surfaces forming the slot into one of a plurality of notches 126 on a bottom surface of the mounting member 106. When the slot 123 receives one of the protrusions 125, the surfaces forming the slot may prevent sliding of the mounting member 106 distally and proximally by holding the protrusion 125 in place. For example, the lip 124 that forms one side of the slot 123, may enter one of the notches 126, and engage a side of the protrusion 125, thus preventing sliding of the mounting member 106. When the protrusion 125 contacts the closed end of the slot 123, and/or the lip 124 makes contact with an end wall 132 of the notch 126, further upward movement of the locking button 114 may cease, and the locking button 114 may occupy a raised position.

To move the mounting member 106 and hypotube 24, and thus, set the relative distance between the penetrating tip 38 of the hypotube 24 and the distal end of the sheath 16, a user may push down on the locking button 114 to free the protrusion 125 from the slot 123. The user may then slide the mounting member 106 relative to the housing 96 to a desired position at which the slot 123 may be aligned with a new protrusion 125. By setting the position of the mounting member 106 relative to the housing 96, the length of the hypotube 24 that extends out from the sheath 16 can be set, thereby setting the penetration depth of the hypotube 24 into the tissue. When the desired penetration depth is reached, the user may release the locking button 114, and the button spring 116 may bring the slot 123 around the new protrusion. Accordingly, the locking button 114 may maintain the set penetration depth until the locking button 114 is once again depressed and the mounting member 106 is moved.

It is contemplated that the notches 126 may have equal thicknesses, so penetration depth may be adjusted in equal increments by moving the locking button 114 between adjacent protrusions 125. Alternatively, one or more of the notches 126 may have a different thickness, so penetration depth can be adjusted in different increments, if desired.

The distances between adjacent notches 126 may be known, thus providing the user with an indication of how far the penetrating tip 38 of the hypotube 24 has moved, with respect to the distal end of the sheath 16, based on the number of notches traversed during movement of the mounting member 106. It is also contemplated that the depth indicator 100 may provide an indication of the position of the penetrating tip 38 of the hypotube 24 relative to the distal end of the sheath 16.

The depth indicator 100 may include a gauge 134 on the housing 96, and a slider 136 (FIG. 12) coupled to a distal end of the mounting member 106. The slider 136 may extend out of the housing 96, and at least a portion of the slider 136 may be positioned over or adjacent to the gauge 134. The position of the slider 136 relative to marks of the gauge 134 may provide an indication of the relative position of the mounting member 106 relative to the housing 96, thereby providing an indication of the relative position of the penetrating tip 38 of the hypotube 24 relative to the distal end of the sheath 16, and providing the penetration depth of the hypotube 24.

Figure 12:
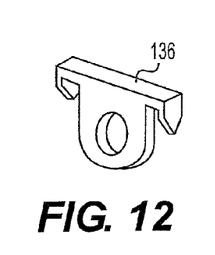
FIG. 12 shows a perspective view of a slider of the injection device in FIG. 7, according to an exemplary embodiment of the present disclosure.

For example, when the slider 136 is positioned at the most proximal mark on the gauge 134, the mounting member 106 may be positioned relative to the housing 96 such that the penetrating tip 38 of the hypotube 24 is positioned at the distal end of the sheath 16. As the mounting member 106 is moved distally relative to the housing 96, exposing a length of the hypotube 24 from the distal end of the sheath 16, the slider 136 may also move distally. The exposed length may be substantially equal to the difference in distance between the most proximal mark on the gauge 134, and a more distal mark at which the slider 136 may now be positioned. Thus, based on movement of the slider 136 along the gauge 134, a user may determine the length of the hypotube 24 exposed from the distal end of the sheath 16, and thus, the penetration depth of the hypotube 24.

The steps for performing procedures using the injection device 90 may be similar to the steps for using the injection device 10. One difference is that once the target area is reached by the distal end of the injection device 90, the user may set and/or adjust the needle penetration depth by depressing the locking button 114. This may release the lip 124 from one of the notches 126. With the lip 124 free, and the opening 122 substantially aligned with the mounting member 106, the user may slide the mounting member 106 relative to the housing 96. The user may slide the mounting member 106 until the depth indicator 100 is positioned on a desired marking on the gauge 134, corresponding to extension of a desired length of the hypotube 24 from the distal end of the sheath 16, which in turn corresponds to a desired needle penetration depth. When the desired length of the hypotube 24 is extended, the user may release the locking button 114, allowing the lip 124 to engage another of the notches 126, thereby fixing the mounting member 106 relative to the housing 96, and thus, fixing the needle penetration depth.

The user may then inject desired and/or consistent amounts of the material 26 into multiple sites at the target area in a manner that is the same or similar to that which has been described above with respect to the embodiment shown in FIGS. 1-6.

Figure 14:
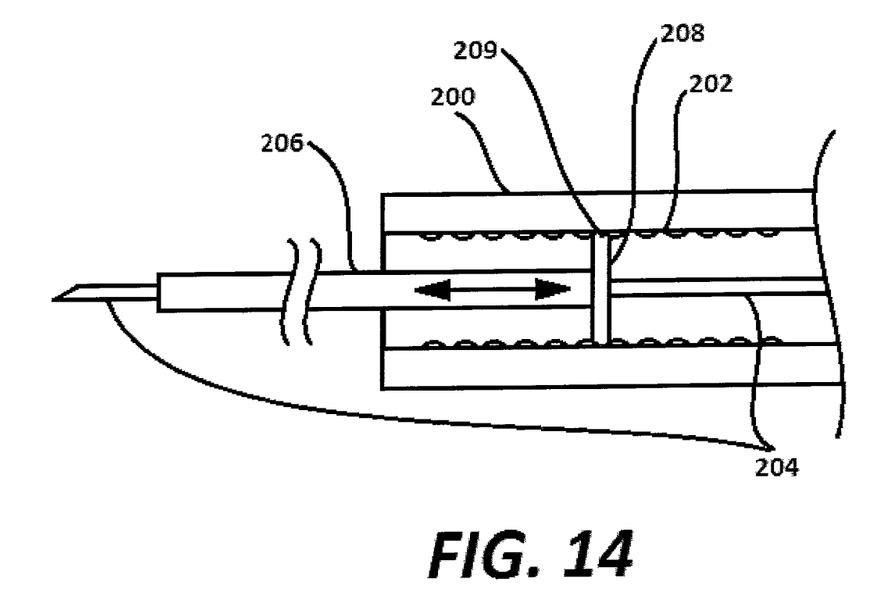
FIG. 14 shows a top view of a portion of another injection device, according to an exemplary embodiment of the present disclosure.

In an alternative embodiment shown in FIG. 14, a base 200, similar to the base 14 or the base 92, may include a plurality of slots 202, arranged in predetermined increments. It is also contemplated that the plurality of slots 202 may be provided within an open cavity in the base 200. A hypotube 204, similar to the hypotube 24, may be coupled to the base 200. A sheath 206, similar to the sheath 16, may be slidably disposed on the hypotube 204, and may be movable with respect to the base 200. The sheath 206 may include a flange 208 at or near its proximal end, distal to an injector (not shown) that may be similar to the injector 12. The flange 208 may include one or more protrusions 209, configured to engage the slots 202, in a snap-fit arrangement that allows selective coupling and decoupling of the flange from the slots 202. A user may adjust positioning of the sheath 206 relative to the hypotube 204, thereby adjusting the length of exposed hypotube 204 at the distal end, by moving the flange 208 out of engagement with one of the slots 202, and into engagement with another one of the slots 202. The user may move the sheath 206 and flange 208 from one of the slots 202 to a proximal slot 202, to expose a desired length of the distal portion of the hypotube 204 from the distal end of the sheath 206. Or the user could move the sheath 206 and flange 208 from one of the slots 202 to a distal slot 202, to cover a desired length of the distal portion of the hypotube 204 with the distal end of the sheath 206.

While principles of the present disclosure are described herein with reference to illustrative embodiments for particular applications, it should be understood that the disclosure is not limited thereto. It should also be understood that aspects of each embodiment described herein may be incorporated into the other embodiments described herein. Also, those having ordinary skill in the art and access to the teachings provided herein will recognize additional modifications, applications, embodiments, and substitution of equivalents all fall within the scope of the embodiments described herein. Accordingly, the disclosure is not to be considered as limited by the foregoing description.

We claim:

1. An injection device, comprising:
a sheath having a distal end;
an injector having an outlet tube movably positioned within the sheath and including a distal portion with a penetrating tip, wherein in a first state, the tip is located a first distance relative to the distal end of the sheath, and in a second state, the tip is located a second distance relative to the distal end of the sheath; and
an adjuster contacting the sheath and having a first orientation and a second orientation different than the first orientation, wherein in the first orientation the adjustor extends radially inwardly into the injector a first distance enabling movement of the tip between the first state and the second state, and in the second orientation the adjustor extends radially inwardly into the injector a second distance, different than the first distance, thereby compressing the sheath about the outlet tube and preventing movement of the tip between the first state and the second state.

2. The injection device of claim 1, wherein the adjuster includes a clamp rotatable with respect to the injector about an axis normal to a longitudinal axis of the sheath.

3. The injection device of claim 2, wherein the clamp includes a screw.

4. The injection device of claim 2, wherein the adjuster includes a roller in contact with the sheath.

5. The injection device of claim 4, wherein, in the first orientation of the adjuster, rotation of the roller moves the sheath relative to the outlet tube.

6. The injection device of claim 1, further a gauge including indicia indicative of an extended length of the outlet tube based on a position of the proximal end of the sheath relative to the gauge.

7. The injection device of claim 1, further including a notched member fixed to the outlet tube.

8. The injection device of claim 7, wherein the adjuster includes a spring member biasing the adjuster into engagement with the notch.

9. The injection device of claim 8, wherein the adjuster includes a button coupled to the spring member.

10. An injection device, comprising:
an injector, including:
a barrel having an internal chamber,
a tube fluidly coupled to the internal chamber,
a plunger slidably disposed in the internal chamber, and
a guiding element coupled to the plunger, wherein the plunger includes a plurality of notches, and the guiding element selectively engages at least one of the plurality of notches;
a sheath extending distally of the infector; and
an adjuster coupled to the injector, the adjuster having a first orientation and a second orientation different than the first orientation, wherein in the first orientation the adjustor extends into the injector a first distance, and in the second orientation the adjustor extends into the injector a second distance and directly contacts the sheath, wherein the second distance is different than the first distance, thereby preventing movement of the tube, wherein at least a portion of the adjustor is rotatable with respect to the injector about an axis normal to a longitudinal axis of the tube.

11. The injection device of claim 10, wherein the plunger includes a shaft, and the plurality of notches are formed on the shaft.

12. The injection device of claim 11, wherein the plurality of notches are evenly spaced along the shaft.

13. The injection device of claim 11, wherein a first plurality of notches are formed on a first side of the shaft, and a second plurality of notches are formed on a second side of the shaft.

14. The injection device of claim 13, wherein spacing of the first plurality of notches is different from spacing of the second plurality of notches.

15. The injection device of claim 11, wherein the guiding element includes a spring clip.

16. The injection device of claim 10, wherein the adjuster includes a screw and a roller, wherein in the second orientation, the tube is compressed between the screw and the roller.

17. An injection device, comprising:
a sheath having a distal end and a proximal end; and an injector coupled to the proximal end of the sheath, the injector having:
  an outlet tube positioned within the sheath and longitudinally moveable relative to the sheath between a first state and a second state different than the first state; and
  an adjuster coupled to and rotatable with respect to the injector about an axis normal to a longitudinal axis of the sheath, wherein in a first orientation the adjustor extends into the injector a first distance, and in the second orientation the adjustor extends into the injector a second distance and directly contacts the sheath, wherein the second distance is different than the first distance.

18. The injection device of claim 17, wherein the adjustor includes a screw.

19. The injection device of claim 18, wherein the adjuster further includes a roller in contact with the sheath.

\* \* \* \* \*